United States Patent [19]

Durrance et al.

[11] Patent Number: 5,446,100

[45] Date of Patent: * Aug. 29, 1995

[54] ENVIRONMENTALLY FRIENDLY POLYMERIC WEB COMPOSITIONS

[75] Inventors: Debra H. Durrance, Lilburn; Philip A. Sasse, Alpharetta, both of Ga.

[73] Assignee: Kimberly-Clark Corporation, Neenah, Wis.

[ * ] Notice: The portion of the term of this patent subsequent to Jun. 8, 2010 has been disclaimed.

[21] Appl. No.: 43,507

[22] Filed: Apr. 6, 1993

Related U.S. Application Data

[60] Continuation of Ser. No. 855,993, Mar. 20, 1992, abandoned, which is a division of Ser. No. 598,277, Oct. 16, 1990, abandoned.

[51] Int. Cl.$^6$ ............... C08L 33/08; C08L 33/02; C08L 23/04
[52] U.S. Cl. .................. 525/221; 428/296; 428/198; 525/227; 525/240
[58] Field of Search ............ 525/221, 240, 227; 428/296, 198

[56] References Cited

U.S. PATENT DOCUMENTS

| | | | |
|---|---|---|---|
| 3,674,896 | 7/1972 | Purcell et al. | 525/57 |
| 4,551,369 | 11/1985 | Belz | 423/37 |
| 4,612,355 | 9/1986 | Belz | 526/65 |
| 4,874,830 | 10/1989 | Saitoh et al. | 526/318.4 |
| 5,063,272 | 11/1991 | Sasse | 524/377 |
| 5,135,979 | 8/1992 | Sasse | 524/377 |
| 5,149,333 | 9/1992 | Sasse | 604/367 |
| 5,217,795 | 6/1993 | Sasse et al. | 428/224 |

*Primary Examiner*—W. Robinson Clark
*Attorney, Agent, or Firm*—Gregory E. Croft

[57] ABSTRACT

The properties of (meth)acrylic ester/(meth)acrylic acid copolymer webs, such as films and nonwovens, are improved by blending the ester/acid copolymer with a copolymer of ethylene and acrylic acid. The copolymer blend provides a polymeric material which is useful for making personal care products such as diapers and feminine pads in that it can be made water-soluble while exhibiting other properties which are necessary for adequate product performance.

21 Claims, No Drawings

ENVIRONMENTALLY FRIENDLY POLYMERIC WEB COMPOSITIONS

This is a continuation application of application Ser. No. 07/855,993 filed on Mar. 20, 1992, now abandoned, which is a divisional of Ser. No. 07/598,277 filed on Oct. 16, 1990, now abandoned.

BACKGROUND OF THE INVENTION

In the production of personal care products, a number of different components and materials are required to construct the products. In the case of diaper manufacture, for example, these components include a backing material, which is a film, and an inner liner, which is typically a nonwoven web. Also, composite structures of synthetic and natural fibers have utility as absorbent media in a variety of personal care products. These various synthetic components are typically made from thermoplastic polymers such as polyethylene or polypropylene. However, with a greater emphasis being placed on protecting the environment today, there is a need to develop materials which are more compatible with existing and developing waste disposal technologies while still delivering the performance consumers have come to expect.

Copolymers of (meth)acrylate esters and (meth)acrylic acid are of environmental interest because of their solubility in alkaline solutions or upon prolonged exposure to moisture, even though they are relatively hydrophobic. Unfortunately, the physical properties which make these materials desirable from an environmental standpoint can make them unsuitable for personal care products. In particular, films made from these polymers in contact with synthetic urine for a period greater than one hour will become hydrated, weak and sticky. This is obviously unacceptable for use in diapers, for example. Films made from these polymers also suffer from a lack of toughness and tear resistance. Films and nonwovens made from these copolymers are somewhat sticky and tend to stick or "block" in roll form. In addition, dimensional stability and aesthetic properties of these materials are also poor.

Therefore there is a need for copolymers of (meth)acrylate esters and (meth)acrylic acid which have modified properties suitable for use as components in personal care products.

SUMMARY OF THE INVENTION

It has now been found that copolymers of (meth)acrylate esters and/or (meth)acrylic acid can be modified with additional materials to provide polymeric webs having improved properties suitable for use in personal care products. More specifically, it has been discovered that copolymers of ethylene and (meth)acrylic acid, when blended with these ester/acid copolymers, impart increased resistance to moisture for webs made therefrom. In addition, the tackiness of such webs is decreased, and dimensional stability and hand are markedly improved. Hence, in one aspect, the invention resides in a composition of matter comprising a polymeric blend of from about 50 to about 90 weight percent of a (meth)acrylate ester/(meth)acrylic acid copolymer and from about 10 to about 50 weight percent of a copolymer of ethylene and (meth)acrylic acid.

In another aspect, the invention resides in a polymeric web comprising a blend of from about 50 to about 90 weight percent of a (meth)acrylate ester/(meth)acrylic acid copolymer and from about 10 to about 50 weight percent of a copolymer of ethylene and (meth)acrylic acid. The relative proportions of the two copolymers will depend upon the desired properties of the product into which they are to be made. For use in making films, for example, it is preferred that the copolymer blend contain from about 65 to about 90 weight percent of an ethyl acrylate/methacrylic acid copolymer and from about 10 to about 20 weight percent of an ethylene/acrylic acid copolymer. For use in making nonwoven webs, such as spunbonded webs, it is preferred that the copolymer blend contain from about 70 to about 80 weight percent of the ethyl acrylate/methacrylic acid copolymer and from about 15 to about 30 weight percent of an ethylene/acrylic acid copolymer.

In a further aspect, the invention resides in an absorbent article having an outer cover, an absorbent core, and an inner liner, wherein any or all of said outer cover, absorbent core and inner liner comprise the webs (nonwoven or film) described herein. Such absorbent articles particularly include diapers and sanitary napkins.

The ethyl acrylate/methacrylic acid copolymer that is most preferred has a 4:1 ratio of the two comonomers by weight. The weight average molecular weight is about 150,000, with a melt flow rate of about 7 grams per 10 minutes, as measured at 170° C. using a 2160 g weight and a 2.1 mm by 8 mm capillary. Clearly, however, many similar copolymers can be prepared that will provide similar attributes and can be substituted for the most preferred copolymer in these compositions. For example, any other (meth)acrylate ester derived from an alcohol having from 1 to 18 carbon atoms can be substituted for all or part of the ethyl acrylate. Such substitutions can lead to enhancement of particular properties for specific material applications. The manufacture of such copolymers is described in U.S. Pat. No. 4,870,148 to RB Kunststoffpatent-Verwertugs AG and Belland AG, both of Switzerland, issued Sep. 26, 1989, which is herein incorporated by reference. Such copolymers are commercially available from Belland AG, and the most preferred copolymer is available as product code "GBC 2620".

The ethylene/acrylic acid copolymers that are most preferred in these blends are high melt index dispersible polymers that are typically 20 percent acrylic acid by weight and 300 to 1300 in melt index. They are dispersible in alkaline water without emulsifiers, but are water-resistant in the acid form. Other suitable ethylene/acrylic acid copolymers which are available contain 3 to 9.5 percent acrylic acid by weight and have a melt index from 2.5 to 13.5. Such copolymers are commercially available from Dow Chemical Company, Midland, Mich. under the tradename PRIMACOR ®, with the most preferred copolymers being those with product code numbers ranging from "5980" to "5990". They are produced by the free radical, high pressure copolymerization of ethylene and acrylic acid in a process similar to that used for producing low-density polyethylene. Ethylene/methacrylic acid copolymers are also suitable for use in these blends. Such copolymers are commercially available from E. I. du Pont, Wilmington, Del., under the tradename NUCREL ™, with grades ranging from 4 to 12 percent methacrylic acid by weight and from 2.5 to 13.5 in melt index, Blends of the two copolymers can be prepared by mixing the desired weight ratio of the copolymer pellets and blending them using any standard equipment commonly used for blending thermoplastic polymers under conditions of heat and high shear. These include the Banbury ® type of intensive production mixer (Farrel Corp, Ansonia, Conn.) and both single- and twin-screw compounding extruders, which can utilize high-shear mixing screws, co-rotating kneading blocks, etc.

In addition to blends containing the two above-mentioned copolymers, other components can be added to further enhance the properties of the resulting material. For example, polyethylene glycol can be added to lower the melt viscosity of these copolymers to a range suitable for meltblown or meltsprayed nonwovens and also improve the flexibility of the resulting webs. The amount of polyethylene glycol added to the copolymer blend can be from about 5 to about 20 weight percent, based on the total weight of the final blend, and a preferred range is from about 10 to about 15 weight percent. Suitable polyethylene glycols are available commercially from Union Carbide Corporation, Tarrytown, N.J., under the tradename CARBOWAX ®; most suitable are product code numbers "3350" and "8000."

Polyethylene can also be added to blends containing the above-mentioned copolymers to improve the softness of the resulting nonwoven webs. The amount of polyethylene added to the copolymer blend can be from about 5 to about 15 weight percent, based on the total weight of the blend. The polyethylene grade must be selected so that the final blend has a melt index suitable for the nonwoven process to be used. Suitable fiber grade polyethylenes are available commercially from Dow Chemical Company, Midland, Mich., under the tradename ASPUN ™. Product code number "6811" is most suitable for blends for spunbond nonwovens and product code numbers "6806" and "6814" are most suitable for blends for meltblown or meltsprayed nonwovens.

Still further improvements to the properties of the webs of this invention, particularly films, can be made by adding certain fillers such as fumed silica, calcium carbonate or talc. Various particulate fillers have been shown to reduce blocking, noise and gloss in the films. Such materials can be added in amounts of from about 2 percent to about 20 weight percent, based on the total weight of the blend. Processing characteristics of the blends for both films and nonwovens can be improved by the incorporation of lubricants or slip agents into the blends. Additives of other types normally used in polymer blends can also be incorporated to provide specific properties as needed, such as antistatic agents, pigments or other colorants, and the like. All of these additive types are generally used in small amounts, usually less than 5 percent.

Films of the two copolymers can be prepared by extrusion of the blend through a linear film die, allowing the film to attenuate under its own weight into a nip between two chilled rolls. Alternatively, an annular die can be used to produce a polymeric tube, which can be attenuated by an air stream to form a film "bubble."

Nonwoven webs of the two copolymers can be prepared by extrusion of the blend through a plurality of capillaries, producing a series of filaments. These filaments can be quenched and then attenuated into fibers by an accelerating gas stream. The fibers can be collected on a moving surface, where they are deposited by the gas stream in a random fashion. Passing the resulting batt through a pair of heated rolls bonds the fibers together into an integral web. Alternatively, a hot gas stream may be used to attenuate and break the filaments in the molten state. These discontinuous fibers can be collected on a moving surface, where they will lay down in a random, entangled manner, producing an integral web. Suitable nonwoven webs include, without limitation, meltblown webs, spunbonded webs, and coform webs (meltblown webs in which a second fiber source, such as cellulose fibers, is blown into the primary meltblown fiber stream prior to deposition onto the collecting surface). All of such webs are known in the nonwovens art.

EXAMPLES

Example 1: Preparation of Copolymer Blend

A blend containing 80 percent by weight of Belland's blended copolymer product designated GBC 2620 WB was prepared. This product is reported to be a copolymer of ethyl acrylate and methacrylic acid in a ratio of 4:1 by weight, respectively. The blended product is reported to contain 1 percent by weight of titanium dioxide and 3 percent by weight of Hostalube ™ FA-1 (Hoescht Celanese, mixed amide of ethylenediamine with palmitic and stearic acids).

To prepare the blend of interest, this product was compounded with 18 percent by weight Primacor ® 5990 (Dow, ethylene-acrylic acid copolymer) and 2 percent by weight of Slip-Quick ® (Synthetic Products Co., fatty amide slip agent). The ingredients were first mixed thoroughly by means of a drum tumbler, and then transferred to an Accurate ® volumetric feeder. The mixture was metered into a Werner & Pfleiderer 30-mm twin-screw compounding extruder for blending. Extruder zones 1 through 6 were set with the following temperature profile (in °C.): 100, 101,110, 121,140, 145; with the lowest temperature being at the feed zone adjacent to the throat of the extruder where the mixture enters and the highest temperature being at the die from which the molten blend exits.

The extruder screw configuration used was a vented, two-stage mixing screw combination of a type typically used for preparing polyolefin blends. Extruder throughput was maintained at ca. 50 pounds/hour. The molten blend was taken off from a four-strand die into a water bath with a dip length of six feet, then through two air knives to remove as much water as possible. The pellets were ejected from a rotating-knife pelletizer directly into a spin dryer to remove the remaining surface moisture before screening and packaging.

Example 2: Preparation of Copolymer Blend Film

A copolymer blend containing 80% GBC 2620 WB, 10% Primacor ® 5990, and 10% Microtuff ® F (Pfizer, surface-treated talc) was blended as in Example 1. The polymer blend was then processed at a rate of 115 pounds/hour through a single-screw extruder with a 3.5 inch diameter, internally-cooled screw (3:1 compression ratio, 24:1 L/D). A flat temperature profile of 260° F. was used in all extruder zones, transfer piping and in the film die. Film was produced using a six-inch diameter annular die with a die gap of 0.042 inches. A bubble was generated with a diameter of 14–18 inches, producing film that varied from 0.0011 to 0.0014 inches in gauge. The film was collected at 84 feet per minute.

Ultimate tensile strengths were determined to be 1868 grams/inch at 220% elongation (machine direction) and 1400 grams/inch at 270% elongation (cross direction). A similarly-prepared film of 100% GBC 2620 WB with the same gauge of 0.0011 inch had ultimate tensile strengths of 2647 grams/inch at 224% elongation (machine direction) and 1274 grams/inch at 365% elongation (cross direction). The films prepared from the described blend show less isotropy, less tendency to block, and better moisture resistance than the film prepared from GBC 2620 WB alone.

Example 3: Preparation of Copolymer Blend Nonwoven Web

A copolymer blend containing 70% GBC 2620 WB, 28% Primacor ® 5990, and 2% Slip-Quick ® was prepared as in Example 1. A nonwoven web was prepared from this blend by means of a spunbond process. The polymer blend pellets were introduced into a single-screw extruder having a screw configuration of a type normally used for extrusion of polyolefins. The molten polymer, at a melt temperature of 340° F., was conveyed from the extruder through a metering pump to a fiber-spinning die. Molten polymer strands exiting the die were quenched, attenuated and formed into a web by controlled streams of high-velocity air. The resulting web was carried by a forming wire through compaction and bonding sections to form a point-bonded spunbond nonwoven.

Webs formed in this manner are dimensionally stable (less than 5% shrinkage) and possess acceptable drape, flexibility and softness. Webs prepared by the same process from GBC 2620 with no additives suffered severe shrinkage (up to 50%), distortion, and increasing rigidity over several weeks. Moisture was found to accelerate these changes.

Example 4: Preparation and Processing of Copolymer Blend With Polyethylene Glycol A copolymer blend containing 80% GBC 2630 AA (a 4.3:1 ethyl acrylate/methacrylic acid copolymer with no additives), 10% Primacor ® 5990, and 10% Carbowax ® 3350 (Union Carbide, polyethylene glycol of molecular weight 3000–3700) was prepared using a ¾" single-screw compounding extruder with a single mixing section and L/D of 26:1. Strands were generated through a dual-strand die at 320° F., allowed to air cool, and pelletized.

This blend was processed through a meltblown apparatus using a ¾" single-screw extruder with an L/D ratio of 26:1. The melt was metered into a meltblown die containing 14 capillaries in a 2" width with a capillary diameter of 0.0145 inch. The extruder zones 1–3 were set for the following temperature profile (in °F.): 136, 257, 342. The die and air were heated to 435° F. Fibers were produced using this apparatus and polymer blend with fiber diameters ranging from 0.01 to 0.04 mm. The fibers were laid down in a random manner on a screen, forming a meltblown web. The level of interfiber adhesion was high, and no further bonding was needed to maintain integrity in the web.

It will be appreciated by those skilled in the art that the foregoing examples, given for purposes of illustration, are not to be construed as limiting the scope of this invention.

We claim:

1. A composition of matter comprising a blend of from about 50 to about 90 weight percent of a copolymer of a (meth)acrylate ester and (meth)acrylic acid and from about 10 to about 50 weight percent of a copolymer of ethylene and (meth)acrylic acid.

2. The composition of claim 1 wherein the (meth)acrylate ester is ethyl acrylate.

3. The composition of claim 2 wherein the (meth)acrylic acid of the ethyl acrylate/(meth)acrylic acid copolymer is methacrylic acid.

4. The composition of claim 3 wherein the (meth)acrylic acid of the ethylene/(meth)acrylic acid copolymer is acrylic acid.

5. The composition of claim 4 wherein the copolymer of ethyl acrylate and methacrylic acid comprises about 80 weight percent ethyl acrylate moieties and about 20 weight percent methacrylic acid moieties.

6. The composition of claim 4 wherein the copolymer of ethylene and acrylic acid comprises about 80 weight percent ethylene moieties and about 20 weight percent acrylic acid moieties.

7. The composition of claim 4 comprising from about 70 to about 90 weight percent of a copolymer of ethyl acrylate and methacrylic acid and from about 10 to about 30 weight percent of a copolymer of ethylene and acrylic acid.

8. The composition of claim 4 comprising from about 80 to about 90 weight percent of a copolymer of ethyl acrylate and methacrylic acid and from about 10 to about 20 weight percent of a copolymer of ethylene and acrylic acid.

9. A polymeric web comprising a blend of from about 50 to about 90 weight percent of a copolymer of a (meth)acrylate ester and (meth)acrylic acid and from about 10 to about 50 weight percent of a copolymer of ethylene and (meth)acrylic acid.

10. The web of claim 9 wherein the (meth)acrylate ester is ethyl acrylate.

11. The web of claim 10 wherein (meth)acrylic acid of the ethyl acrylate/(meth)acrylic acid copolymer is methacrylic acid.

12. The web of claim 11 wherein the (meth)acrylic acid of the copolymer of ethylene and (meth)acrylic acid is acrylic acid.

13. The web of claim 12 wherein the copolymer of ethyl acrylate and methacrylic acid comprises about 80 weight percent ethyl acrylate moieties and about 20 weight percent methacrylic acid moieties.

14. The web of claim 12 wherein the copolymer of ethylene and acrylic acid comprises about 80 weight percent ethylene moieties and about 20 weight percent acrylic acid moieties.

15. The web of claim 12 comprising from about 70 to about 90 weight percent of a copolymer of ethyl acrylate and methacrylic acid and from about 10 to about 30 weight percent of a copolymer of ethylene and acrylic acid.

16. The web of claim 12 comprising from about 80 to about 90 weight percent of a copolymer of ethyl acrylate and methacrylic acid and from about 10 to about 20 weight percent of a copolymer of ethylene and acrylic acid.

17. A nonwoven web comprising a blend of from about 50 to about 90 weight percent of a copolymer of ethyl acrylate and methacrylic acid and from about 10 to about 50 weight percent of a copolymer of ethylene and acrylic acid, wherein said copolymer of ethyl acrylate and methacrylic acid comprises about 80 weight percent ethyl acrylate moieties and about 10 weight percent methacrylic acid moieties and wherein said copolymer of ethylene and acrylic acid comprises about 80 weight percent ethylene moieties and about 20 weight percent acrylic acid moieties.

18. The nonwoven web of claim 17 comprising a blend of from about 70 to about 80 weight percent of a copolymer of ethyl acrylate and methacrylic acid and from about 15 to about 30 weight percent of a copolymer of ethylene and acrylic acid.

19. The nonwoven web of claim 17 wherein said web is a meltblown web.

20. The nonwoven web of claim 17 wherein said web is a spunbonded web.

21. The nonwoven web of claim 17 wherein said web is a coform web.

* * * * *